(12) United States Patent
Yan et al.

(10) Patent No.: US 12,339,257 B2
(45) Date of Patent: Jun. 24, 2025

(54) DEVICE FOR LOW STRESS TRIAXIAL TESTING

(71) Applicant: Tianjin University, Tianjin (CN)

(72) Inventors: Yue Yan, Tianjin (CN); Jiachong Ma, Tianjin (CN); Dengfeng Fu, Tianjin (CN)

(73) Assignee: Tianjin University, Tianjin (CN)

( * ) Notice: Subject to any disclaimer, the term of this patent is extended or adjusted under 35 U.S.C. 154(b) by 309 days.

(21) Appl. No.: 18/303,352

(22) Filed: Apr. 19, 2023

(65) Prior Publication Data

US 2023/0366797 A1 Nov. 16, 2023

(30) Foreign Application Priority Data

May 11, 2022 (CN) .......................... 202221209286.0

(51) Int. Cl.
*G01N 3/08* (2006.01)
*G01N 3/06* (2006.01)
*G01N 33/24* (2006.01)
*G01N 3/12* (2006.01)

(52) U.S. Cl.
CPC ................. *G01N 3/08* (2013.01); *G01N 3/06* (2013.01); *G01N 33/24* (2013.01); *G01N 3/12* (2013.01); *G01N 2203/0019* (2013.01); *G01N 2203/0048* (2013.01); *G01N 2203/023* (2013.01); *G01N 2203/0232* (2013.01); *G01N 2203/0256* (2013.01); *G01N 2203/0284* (2013.01)

(58) Field of Classification Search
CPC .............. G01N 3/08; G01N 3/06; G01N 3/12; G01N 33/24; G01N 2203/0019; G01N 2203/023; G01N 2203/0048; G01N 2203/0232; G01N 2203/0256; G01N 2203/0284
See application file for complete search history.

(56) References Cited

U.S. PATENT DOCUMENTS

2022/0236156 A1\* 7/2022 Cai .................... G01N 15/0255
2023/0033460 A1\* 2/2023 Kong ....................... G01N 3/24

FOREIGN PATENT DOCUMENTS

CN 216144663 U \* 3/2022

\* cited by examiner

*Primary Examiner* — Jonathan M Dunlap
(74) *Attorney, Agent, or Firm* — Hemisphere Law, PLLC; Zhigang Ma

(57) ABSTRACT

A device for a low stress triaxial test includes a test platform; a pressure chamber disposed on the test platform; a base disposed on the pressure chamber and fixed to the test platform; a support disposed on the test platform; a servo motor disposed on the support; a loading piston connected to the servo motor and penetrating into the pressure chamber; an axial force sensor disposed on the loading piston; a top cap detachably connected to the loading piston and covering the sample; a first pipeline connected to the base and passing through the test platform to connect with a measurement system; a second pipeline connected to the pressure chamber and passing through the test platform to connect with a confining pressure control system; and a third pipeline connected to the first pipeline and the top cap. The device can ensure the accuracy and authenticity of test results.

3 Claims, 2 Drawing Sheets

DEVICE FOR LOW STRESS TRIAXIAL TESTING

FIELD OF THE DISCLOSURE

The disclosure relates to the technical field of geotechnical engineering testing, in particular to a device for a low stress triaxial testing.

BACKGROUND OF THE DISCLOSURE

When conducting a low stress triaxial test on sand, silt, and saturated soft soil, first of all, due to soft nature of soil samples, it is difficult to form soil samples during a sample preparation process, and it is easy to disturb the soil samples during the sample preparation process, resulting in inaccurate test results, therefore, a preparation process of the sand, the silt, and the saturated soft soil is very difficult. Secondly, when conducting the low stress triaxial test, due to small applied confining pressure, accuracy of results of the low stress triaxial test is extremely susceptible to factors such as rubber film constraints, sample self-weights, piston self-weights and friction, sample top cap self-weights, hydrostatic pressure in a pressure chamber, end constraints and friction between the top cap and a base, and vacuum added in advance during the sample preparation progress. In other words, compared to traditional triaxial tests, the accuracy of the results of the low stress triaxial test is very easily affected, small disturbance and errors can have a significant impact on the low stress triaxial test, therefore, above factors of the disturbance cannot be ignored. At present, there are mainly following problems in a rubber membrane of a geotechnical triaxial test: (1) wrinkling and buckling of the rubber membrane; (2) embedding of the rubber membrane; and (3) damage of the rubber membrane. The wrinkling of the rubber membrane can induce initial horizontal tensile strain and axial strain in the rubber membrane, thereby affecting volumetric strain measurement results of the soil samples. Therefore, there is an urgent need for a device for the low stress triaxial test that can reduce the disturbance of the external factors to the low stress triaxial test and ensure the accuracy and authenticity of the measurement results of the low stress triaxial test.

SUMMARY OF THE DISCLOSURE

A purpose of the disclosure is to overcome shortcomings of related art described above, aiming to provide a device for a low stress triaxial test that reduces disturbance of external factors to the low stress triaxial test and can ensure accuracy and authenticity of measurement results of the low stress triaxial test.

To achieve the purpose, the disclosure is implemented through following technical solutions.

A device for a low stress triaxial test, includes: a pressure chamber, a test platform, a base, a support, a servo motor, a loading piston, an axial force sensor, a top cap, a first pipeline, a second pipeline, a third pipeline, a measurement system, a confining pressure control system, a pore pressure sensor, a pore water pressure valve, a deformation measuring device, an inflatable valve, and a water filling valve;

the pressure chamber is disposed on an upper end surface of the test platform; the base is disposed on a bottom of the pressure chamber and fixed to the test platform; and the base is configured (i.e., structured and arranged) to place a sample coated with a super-light clay membrane; the support is disposed on the upper end surface of the test platform, and the support is higher than the pressure chamber; the servo motor is disposed on a top of the support; the loading piston is connected to the servo motor and penetrates into the pressure chamber; the axial force sensor is disposed on the loading piston; the top cap is detachably connected to a bottom end of the loading piston and configured to cover the sample; the first pipeline passes through the test platform and the base; the measurement system is connected to the first pipeline; the second pipeline passes through the test platform and base and is connected to the pressure chamber; the confining pressure control system is connected to the second pipeline; the third pipeline penetrates through the base, an end of the third pipeline is connected to the first pipeline, and another end of the third pipeline is connected to the top cap; the pore pressure sensor is disposed on the first pipeline; the pore water pressure valve is disposed on the first pipeline; the deformation measuring device is disposed on the second pipeline; the inflatable valve is disposed on the second pipeline; and the water filling valve is disposed on the third pipeline; the top cap and the base are provided with through-holes connected to pipelines (i.e., the top cap is provided with the through-holes connected to the third pipeline, and the base is provided with the through-holes connected to the first pipeline) and facing towards the sample; silicone grease, a permeable stone and a filter paper are sequentially arranged between the top cap and the sample from top to bottom in that order; and silicone grease, a permeable stone and a filter paper are sequentially arranged between the base and the sample from bottom to top in that order.

In an embodiment, the sample is made from a sampling cylinder in a cylindrical shape, the sampling cylinder includes an inner shell and an outer shell, a surface roughness of each of the inner shell and the outer shell is less than 40 micrometers ($\mu$); the inner shell is divided into three parts and is arranged inside the outer shell to define a gap configured to fasten the super-light clay membrane; inner and outer surfaces of the inner shell and an inner surface of the outer shell are coated with lubricating oil; and a bottom of the outer shell is fixedly provided with foot blades.

In an embodiment, ends of the base and the top cap facing towards the sample are made of a propylene laminate.

Compared to the related art, the disclosure has following beneficial effects.

During a test sampling process, the disclosure can avoid the disturbance caused by a film loading process to a sample preparation process, and the lubricating oil applied to the outer shell and the inner shell of the sampling cylinder can ensure that the disturbance to the super-light clay membrane and the sample is reduced during a sample extraction process. The silicone grease applied on surfaces of the base and the top cap can reduce impact of friction on the low stress triaxial test, and the base and the top cap with a plane larger than the sample can uniformly deform the sample. The servo motor used to control the loading piston can avoid the disturbance caused by the self-weight and the friction on the sample. The confining pressure control system is used to provide stable confining pressure, and a confining pressure medium is compressed gas, which can ensure the confining pressure of the sample along a height direction of the sample being consistent and provide stable low confining pressure for the sample, with high precision in the confining pressure control to achieve the simulation of a stress environment of the low confining pressure of the soil.

Figure 1:
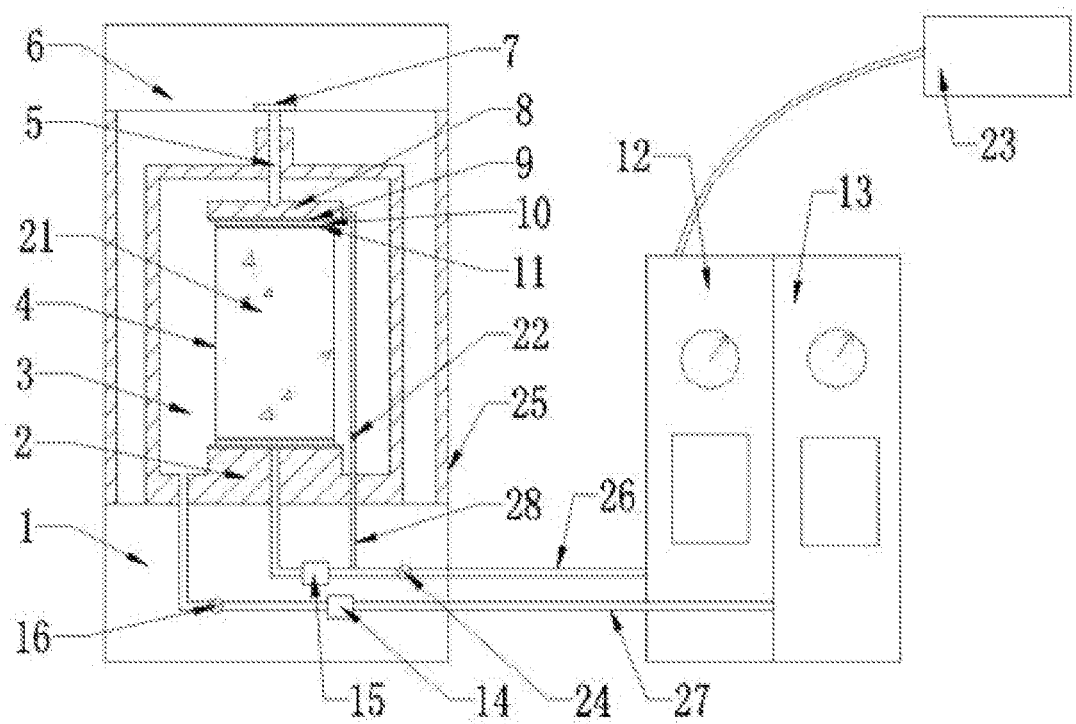
FIG. 1 is a structural schematic diagram of a device for a low stress triaxial test according to an embodiment of the disclosure.

REFERENCE NUMERALS 1. test platform, 2. base, 3. pressure chamber, 4. super-light clay membrane, 5. loading piston, 6. servo motor, 7. axial force sensor, 8. top cap, 9. silicone grease, 10. porous stone, 11. filter paper, 12. measurement system, 13. confining pressure control system, 14. deformation measuring device, 15. pore pressure sensor, 16. inflatable valve, 17. sampling cylinder, 18. inner shell, 19. outer shell, 20. foot blades, 21. sample, 22. water filling valve, 23. computer, 24. pore water pressure valve, 25. support, 26. first pipeline, 27. second pipeline, 28. third pipeline.

DETAILED DESCRIPTION OF EMBODIMENTS

The disclosure will be described in detail below with reference to drawings and in combination with embodiments.

Figure 2:
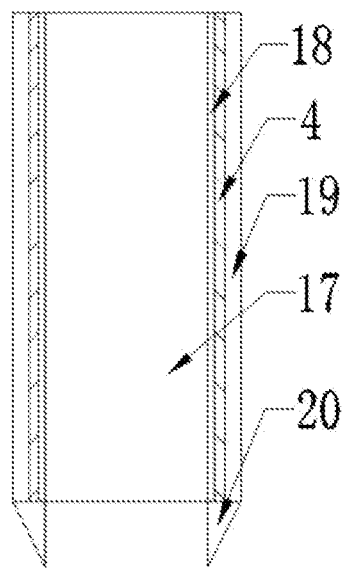
FIG. 2 is a structural diagram of a sampling cylinder according to an embodiment of the disclosure.
Figure 3:
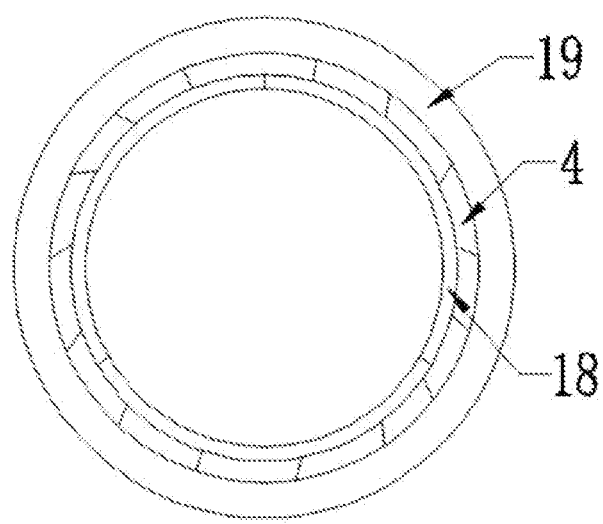
FIG. 3 is a top view of the sampling cylinder of FIG. 2.

As shown in FIGS. 1 to 3, a device for low stress triaxial test includes a pressure chamber 3. The pressure chamber 3 placed on a fixed upper end surface 2 of a test platform 1. A sample 21 coated with a super-light clay membrane 4 is placed on the base 2. The upper end surface of the test platform 1 has a support 25 that is higher than the pressure chamber 3. Top of the support 25 is provided with a servo motor 6. The servo motor 6 is connected with a loading piston 5 that penetrates the pressure chamber 3. The loading piston 5 is provided with an axial force sensor 7. A bottom end of the loading piston 5 is detachably provided with a top cap 8 that can cover the sample 21. The base 2 is provided with a first pipeline 26, a second pipeline 27, and a third pipeline 28. The first pipeline 26 is connected to the base 2 and passes through the test platform 1, the first pipeline 26 is connected to a measurement system 12, and the first pipeline 26 is provided with a pore pressure sensor 15 and a pore water pressure valve 24. The second pipeline 27 is connected to the pressure chamber 3 and passes through the test platform 1, the second pipeline 27 is connected to a confining pressure control system 13, and the second pipeline 27 is provided with a deformation measuring device 14 and an inflatable valve 16. One end of the third pipeline 28 is connected to the first pipeline 26, another end is connected to the top cap 8, and the third pipeline 28 is provided with a water filling valve 22. Both the top cap 8 and the base 2 are provided with through-holes connected to pipelines and facing the sample 21. Between the top cap 8 and the sample 21, silicone grease 9, a porous stone 10, and a filter paper 11 are sequentially arranged from top to bottom. Between the base 2 and the sample 21, the silicone grease 9, the porous stone 10, and the filter paper 11 are sequentially arranged from bottom to top.

In an embodiment, the sample 21 is made from a sampling cylinder 17 in a cylindrical shape. The sampling cylinder 17 includes an inner shell 18 and an outer shell 19. A surface roughness of each of the inner shell 18 and the outer shell 19 is less than 40 micrometers (μm). The inner shell 18 is divided into three parts and is arranged inside the outer shell 19 to define a gap configured to fasten the super-light clay membrane 4. Inner and outer surfaces of the inner shell 18 and an inner surface of the outer shell 19 are coated with lubricating oil. A bottom of the outer shell 19 is fixedly provided with foot blades 20. The sampling cylinder 17 is inserted into soil through the foot blades 20 at bottom. After the inner shell 18 is filled with soil, it is slowly pushed out of the outer shell 19 along with the sample 21 and the super-light clay membrane 4, then the divided inner shell 18 is peeled off from the outside of the sample 21. The inner and outer surfaces of the inner shell 18 coated with lubricating oil can smoothly separate the inner shell 18 from the sample 21 and the super-light clay membrane 4, allowing the sample 21 to completely enter the super-light clay membrane 4. Inner surface of the outer shell 19 is coated with the lubricating oil to smoothly separate the super-light clay membrane 4 from the outer shell 19.

In an embodiment, the silicone grease 9, the permeable stone 10 and the filter paper 11 are sequentially arranged between the top cap 8 and the sample 21 from top to bottom in that order. The silicone grease 9, the permeable stone 10 and the filter paper 11 are sequentially arranged between the base 2 and the sample 21 from bottom to top in that order. The silicone grease 9 includes Shin-etsu silicone grease KS636. The silicone grease 9 has characteristics of small friction coefficient, strong bearing capacity, strong water resistance and corrosion resistance, thereby reducing the friction and the disturbance to the sample 21.

In an embodiment, ends of the base 2 and the top cap 8 facing towards the sample 21 are made of a propylene laminate. A smooth surface can reduce the disturbance of the base 2 and the top cap 8 to the sample and uniformly deform the sample.

The deformation measuring device 14 in the disclosure is used to measure changes in a volume of gas in the pressure chamber 3. When the confining pressure control system 13 fills the pressure chamber 3 with a constant amount of air pressure, the subsequently supplemented gas volume of the confining pressure control system 13 is a deformation amount of the sample 21. The deformation measuring device 14 obtains the deformation amount by measuring data of the subsequently supplemented gas volume; the axial force sensor 7 is disposed between the servo motor 6 and the loading piston 5, with a measurement accuracy of ±4.5 newtons (N). In this embodiment, the axial force sensor 7 is an axial pressure sensor LQ-102 with high precision; the pore pressure sensor 15 has a measurement range of 10 $kilo_{pascal}$ (kPa) and a measurement accuracy of 0.1%. In this embodiment, the pore pressure sensor 15 is a pore water pressure sensor CY303 with high precision. The disclosure aims at the consolidated undrained shear low stress triaxial test of saturated undisturbed sand, and specific test steps are as follows.

(1) The pore water pressure valve 24 and the measurement system 12 are opened, because the base 2 is provided with the through-holes connected to the first pipeline 26 and facing towards the sample 21. Opening the pore water pressure valve 24 and the measurement system 12 allows for water filling and exhaust of the through-holes of the base 2. After the exhaust is completed, the silicone grease 9, the porous stone 10, and the filter paper 11 are sequentially placed on the base 2 in that order to form a water film on the porous stone 10.

(2) The sampling cylinder 17 is opened, the inner shell 18 is removed, an appropriate amount of lubricating oil is applied to both the inner wall of the outer shell 19 and the inner and outer walls of the inner shell 18, and then the super-light clay film 4 is attached to the inner wall of the outer shell 19 slowly. The inner shell 18 is installed, so that the super-light clay membrane 4 is sandwiched between the inner shell 18 and the outer shell 19. The sampling cylinder 17 is inserted into the soil for sampling slowly. After the sampling is completed, the inner shell 18 together with the super-light clay membrane 4 and the internal sample 21 is taken out, and it is placed on the filter paper 11 of the base 2. Finally, the inner shell 18 is taken out. Then the sample 21 is placed inside the super-light clay membrane 4 and placed on the base 2. The interior of the super-light clay material is filled with an elastic structure, which makes it have good elasticity and elastic recovery, easy to shape, strong viscosity, high tensile strength, high adhesion, strong plasticity and adhesion, and can be well attached to the sample 21, deformed with the sample 21, with high compatibility.

(3) The filter paper 11, the porous stone 10, and the silicone grease 9 are sequentially placed on an upper end of the sample 21 in that order, and then 4-5 rubber bands are wrapped around two ends of the super-light clay membrane 4 to seal the sample 21, thus, the filter paper 11, the porous stone 10 and the silicone grease 9 at upper and lower ends of the sample 21 and the sample 21 are integrated into a whole. The water filling valve 22 is opened, the top cap 8 is filled and exhausted. After the exhaust is completed, waiting until a layer of water film is formed on the lower surface of the top cap 8. The top cap 8 is pressed onto the porous stone 10 at the upper end of the sample 21 gently.

(4) The pressure chamber 3 is placed on the test platform 1. Before placing, the loading piston 5 is pushed towards an upper end to avoid contacting the sample 21. After installing the pressure chamber 3, the loading piston 5 is dropped onto the top cap 8 gently, and then the pressure chamber 3 is fixed on the test platform 1.

(5) The loading piston 5 is connected to the servo motor 6, and then a switch of the confining pressure control system 13 and the inflatable valve 16 is opened to inject a constant amount of compressed air into the pressure chamber 3. After setting a fixed confining pressure, the confining pressure and pore pressure are cleared, the ambient pressure is applied to make the sample 21 subjected to equal confining pressure in all directions. The pore water pressure valve 24 is opened until the sample 21 is pressurized, drained, and consolidated. The pore water pressure is recorded through the computer 23 connected to the measurement system 12. The servo motor 6 applies an axial force to shear the sample 21, and the computer 23 records data such as axial displacement. When the sample 21 meets the damage criteria, the test is stopped.

The above is only embodiments of the disclosure and is not intended to limit the disclosure. Any modifications, equivalent replacements, improvements, etc. made within spirits and principles of the disclosure should be included in protection scope of the disclosure.

What is claimed is:

1. A device for a low stress triaxial test, comprising:
a test platform;
a pressure chamber, disposed on an upper end surface of the test platform;
a base, disposed on a bottom of the pressure chamber and fixed to the test platform; wherein the base is configured to place a sample coated with a clay membrane;
a support, disposed on the upper end surface of the test platform, wherein the support is higher than the pressure chamber;
a servo motor, disposed on a top of the support;
a loading piston, connected to the servo motor and penetrating into the pressure chamber;
an axial force sensor, disposed on the loading piston;
a top cap, detachably connected to a bottom end of the loading piston and configured to cover the sample;
a first pipeline, passing through the test platform and the base;
a measurement system, connected to the first pipeline;
a second pipeline, passing through the test platform and base and connected to the pressure chamber; and
a confining pressure control system, connected to the second pipeline;
a third pipeline, penetrating through the base, wherein an end of the third pipeline is connected to the first pipeline, and another end of the third pipeline is connected to the top cap;
a pore pressure sensor, disposed on the first pipeline;
a pore water pressure valve, disposed on the first pipeline;
a deformation measuring device, disposed on the second pipeline;
an inflatable valve, disposed on the second pipeline; and
a water filling valve, disposed on the third pipeline;
wherein the top cap and the base are provided with through-holes connected to pipelines and facing towards the sample; silicone grease, a permeable stone and a filter paper are sequentially arranged between the top cap and the sample from top to bottom in that order; and silicone grease, a permeable stone and a filter paper are sequentially arranged between the base and the sample from bottom to top in that order.

2. The device for the low stress triaxial test according to claim 1, wherein the sample is made from a sampling cylinder in a cylindrical shape, the sampling cylinder comprises an inner shell and an outer shell, a surface roughness of each of the inner shell and the outer shell is less than 40 micrometers (μm); the inner shell is divided into three parts and is arranged inside the outer shell to define a gap configured to fasten the clay membrane; inner and outer surfaces of the inner shell and an inner surface of the outer shell are coated with lubricating oil; and a bottom of the outer shell is fixedly provided with foot blades.

3. The device for the low stress triaxial test according to claim 1, wherein ends of the base and the top cap facing towards the sample are made of a propylene laminate.

\* \* \* \* \*